United States Patent [19]

Lamberti

[11] 4,144,323

[45] Mar. 13, 1979

[54] NOVEL ANTICALCULUS COMPOSITIONS

[75] Inventor: Vincent Lamberti, Upper Saddle River, N.J.

[73] Assignee: Lever Brothers Company, New York, N.Y.

[21] Appl. No.: 916,032

[22] Filed: Jun. 15, 1978

[51] Int. Cl.² ............................................. A61K 7/16
[52] U.S. Cl. ....................................... 424/54; 424/49
[58] Field of Search ................................. 424/49–58

[56] References Cited

U.S. PATENT DOCUMENTS

| | | | |
|---|---|---|---|
| 4,022,880 | 5/1977 | Vinson et al. | 424/49 |
| 4,082,841 | 4/1978 | Pader | 424/50 |

FOREIGN PATENT DOCUMENTS

| | | |
|---|---|---|
| 959764 | 12/1974 | Canada. |
| 71-00701 | 8/1972 | South Africa. |
| 1290627 | 9/1972 | United Kingdom. |
| 1296952 | 11/1972 | United Kingdom. |
| 1373001 | 11/1974 | United Kingdom. |
| 1373003 | 11/1974 | United Kingdom. |

*Primary Examiner*—Shep K. Rose
*Attorney, Agent, or Firm*—James J. Farrell; Melvin H. Kurtz; Kenneth F. Dusyn

[57] ABSTRACT

A method and compositions for retarding plaque and calculus by use of a zinc compound which is substantially less astringent than other zinc compounds typically utilized are disclosed. Zinc salts of carboxymethyloxysuccinic acid are effective anticalculus and antiplaque agents and have been shown to be substantially less astringent than other typically used zinc compounds.

14 Claims, No Drawings

NOVEL ANTICALCULUS COMPOSITIONS

The present invention relates generally to the field of agents useful in the preparation of oral products, such as toothpaste and mouthwashes. The use of the compositions of this invention results in control and retardation of both plaque and calculus by means of a more pleasant tasting, less astringent zinc compound.

Dental plaque is the layer or deposit which forms on the surface of teeth if one refrains from brushing for several days or brushes inadequately. It consists primarily of closely matted microorganisms embedded in a proteinaceous matrix of uncertain origin (but generally considered to be at least partially salivary) and contains epithelial cells and leucocytes. It is believed that calculus in turn is formed by calcification of plaque. Calculus is a hard deposit of calcium phosphate, similar in composition to hydroxyapatite. Nucleation and growth of calcium phosphate crystals must occur before a concrete deposit can result; if it is possible to inhibit this process, then the partially calcified deposits can be removed by ordinary brushing. One such method of inhibition involves the use of a material which can adsorb on the crystals and prevent growth. Pyrophosphates have been used for this purpose, but these materials are subject to degradation by bacterial phosphatases in the mouth. Pader (U.S. application Ser. No. 374,351, now U.S. Pat. No. 4,082,841) found the zinc ion effective against calculus, but due to the astringency of zinc, Pader recommended that only insoluble zinc salts be used in formulating a product. This presents a problem in formulating a mouthwash or a clear toothpaste, where an insoluble salt would be incompatible with the formulation of the product.

Zinc compounds are well known for use in oral products. For example, U.S. Pat. No. 3,622,662 discloses the use of zinc oxide or zinc phosphate as well as selected other phosphates to stabilize a dental cream. In addition, the composition may include an astringent such as zinc sulfate or zinc chloride. U.S. Pat. No. 3,624,199 also contains zinc oxide and zinc sulfate for generally the same purposes. U.S. Patent 4,082,841 contains zinc salts in combination with an enzyme.

Zinc salts are disclosed as anticalculus agents in the aforementioned U.S. application Ser. No. 374,351, now U.S. Pat. No. 4,082,841. U.S. Pat. No. 4,022,880 discloses zinc salts in combination with an antibacterial agent which is effective against calculus plaque. This patent utilizes water-soluble zinc salts and outlines several attempts to retard accumulation of dental calculus by means of zinc salts. Additionally, U.S. Patent Application Ser. No. 849,046 also utilizes zinc in combination with tetradecylamine to retard plaque and Application Ser. No. 840,357 utilizes soluble zinc type compounds as anticalculus agents. The art has generally approached the problem of plaque control by utilizing zinc compounds both soluble and insoluble. One of the major problems with the use of zinc is its high astringency. Accordingly, insoluble zinc compounds provide some plaque and/or calculus reduction and less astringency simply because they are insoluble, whereas more soluble zinc compounds provide better reduction but more astringency due to their solubility. While known to be an effective agent to prevent or control calculus and/or plaque, a dichotomy has arisen as to the consumer acceptability of products containing zinc because of its astringency. Thus, it can be seen that it would be extremely valuable to achieve a balance, i.e. a compound which would provide a sufficient amount of zinc to effectively control or retard plaque and calculus without being present at so high a level that the astringency is unacceptable and yet being soluble enough to easily prepare mouthwashes without the problem of precipitation or unsightly appearance both of which problems can result from a completely insoluble compound.

Accordingly, an object of the present invention is to provide a method and compositions for controlling or substantially reducing plaque while retaining acceptable astringency levels with a compound which is sufficiently soluble to result in consumer acceptable products.

Other objects and advantages will appear as the description proceeds.

The attainment of the above objects is made possible by the instant invention which includes a relatively non-astringent composition for controlling plaque and/or calculus and which has good consumer acceptability by use of a zinc salt having the formula

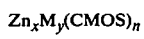

wherein n is 1 or 2 and when n is 1, x and y are both 1 and M is $H^+$, $Na^+$, $K^+$, $Li^+$, $NH_4^+$ or a $C_{10}$ to $C_{18}$ alkyl substituted ammonium cation; when n is 2, x and y are independently 1 or 2 and the sum of $x + y$ is 3 and M is $Ca^{++}$, $Mg^+$ or $Zn^{++}$ as well as mixtures or hydrates of any of these salts; and wherein CMOS is the tri-anion of carboxymethyloxysuccinic acid, i.e.

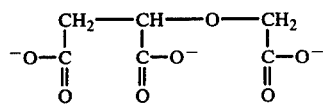

The subject invention encompassing novel compositions and methods for the control of plaque and calculus overcomes one or more of the disadvantages of the prior art heretofore described. It is accompanied by the advantage that these gingival conditions may be controlled with greater ease while using zinc in a form which is substantially less astringent than heretofore utilized.

DESCRIPTION OF THE INVENTION

It has now been found that satisfactory anticalculus and antiplaque activity can be obtained with zinc carboxymethyloxysuccinate (i.e. $Zn_3(CMOS)_2$, abbreviated as zinc CMOS), a compound soluble in water yet less astringent than traditional soluble zinc salts. It is thought that zinc CMOS is less astringent because the CMOS tri-anion is a complexing agent and keeps most of the zinc cation in the complexed form. On the other hand, zinc chloride or zinc sulfate ionize almost completely. Despite the complexing action of CMOS a reversible equilibrium exists so that sufficient free zinc is released in the mouth to be effective against calculus and plaque.

Zinc CMOS [$Zn_3(CMOS)_2$] is a salt of carboxymethyloxysuccinic acid:

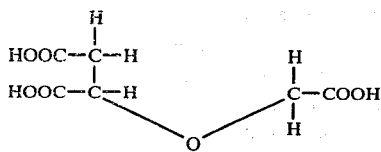

The preparation and characteristics of CMOS compounds generally are described in U.S. Pat. No. 3,914,297. The zinc salt is prepared as follows:

Sodium CMOS ($Na_3CMOS$) is converted to CMOS acid by ion exchange. A polystyrene-sulfonic acid resin, trade name Permuttit Q, is used; a solution of $Na_3CMOS$ is run through the column and eluted with water. A sample of the resultant acid obtained by evaporation of the eluate in vacuo is titrated with sodium hydroxide and found to be 91.8% CMOS acid; the remainder, largely water.

126.6 g (0.60 moles) of CMOS acid are dissolved in 546 ml water at room temperature. 73.3 g of zinc oxide is added over a period of 15 minutes, with the pH rising from 2.0 to 4.0. The mixture is heated in a water bath to 65° C. for one hour after the zinc oxide addition. The solution is then cooled slowly to room temperature and filtered to remove insoluble impurities. The filtrate is then freeze-dried. 179.4 g of zinc CMOS is recovered which is shown by analysis to contain 32.04% zinc and 6.8% water. Theoretically the dihydrate should contain 32.16% zinc and 5.90% water; the trihydrate, 31.24% zinc and 8.6% water. The recovered product may be a mixture of di and tri-hydrates, and may contain some absorbed surface water.

Zinc CMOS solution is titrated with sodium hydroxide and precipitation is noted at pH 6.7. Any liquid product formulated with zinc CMOS should have a pH less than about 6.7 to insure solubility of the compound.

The other zinc salts of the invention, namely $Zn_xM_y(CMOS)_n$, as previously defined, may be prepared using the same procedure as above but using the designated ratio of ZnO to carboxymethyloxysuccinic acid in a first reaction step. The remaining unneutralized carboxyl groups of carboxymethyloxysuccinic acid are then neutralized to the desired pH, usually in the range of about 3 to 8, with an aqueous solution or slurry of an alkaline reagent which may be LiOH, NaOH, KOH, $Ca(OH)_2$ $Mg(OH)_2$ and $NH_4OH$ or selected $C_{10}$ to $C_{18}$ alkyl amines. If the end product is insoluble in the reaction mixture, it may be isolated by filtration. The corresponding carbonates and bicarbonates of the aforesaid alkaline reagents, where appropriate, may also be used in place of the hydroxylic forms. Likewise, CaO and MgO may be used in place of the hydroxide forms. The resulting mixed zinc salts may be isolated as previously described for $Zn_3(CMOS)_2$. Preferred cations for M, in addition to zinc, are sodium, potassium and ammonium and hydrogen.

Mixtures of the zinc salts of the invention, i.e. $Zn_3(CMOS)_2$ and $Zn_xM_y(CMOS)_n$ may also be used and may be prepared directly as a mixture by using the above procedure described for $Zn_xM_y(CMOS)_n$ and the appropriate molar ratio of ZnO and alkaline reagents to carboxymethyloxysuccinic acid. Isolation of the mixed zinc salts is the same as previously described.

The compounds of this invention are exemplified by the following formulae:

ZnH(CMOS)-zinc hydrogen carboxymethyloxysuccinate
$Zn_3(CMOS)_2$-tri-zinc carboxymethyloxysuccinate
ZnNa(CMOS)-zinc sodium carboxymethyloxysuccinate
ZnLi(CMOS)-zinc lithium carboxymethyloxysuccinate
ZnK (CMOS)-zinc potassium carboxymethyloxysuccinate
$ZnNH_4$ (CMOS)-zinc ammonium carboxymethyloxysuccinate
$Zn[CH_3(CH_2)_{11}-NH_3]$(CMOS)-zinc n-dodecylammonium carboxymethyloxysuccinate

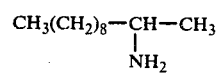
$Zn[CH_3(CH_2)_9-CH-CH_3]$(CMOS)-zinc 2-dodecylammonium carboxymethyloxysuccinate $Zn_2Ca(CMOS)_2$-di-zinc calcium carboxymethyloxysuccinate
$ZnMg_2(CMOS)_2$-zinc di-magnesium carboxymethyloxysuccinate.

As previously stated, mixtures of salts as well as their hydrates or mixtures of hydrates may be used.

The $C_{10}$ to $C_{18}$ alkyl amine may be either a primary amine with the $NH_2$ group on the terminal carbon atoms as for example $CH_3(CH_2)_{15}-NH_2$ or an internal primary amine with the $NH_2$ group remote from the terminal carbon atom as

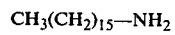

It will be understood, that although species such as $Zn_3(CMOS)_2$, $Zn_2Ca(CMOS)_2$ and $Zn_2Mg(CMOS)_2$ have been described as a monomeric species and in the compositions of this invention such monomeric species predominate, that polymeric forms may also be present in which the molar ratio of $Zn^{++}$ plus other divalent cation present to the carboxymethyloxysuccinic trianion is in the ratio of about 3/2.

ANTIPLAQUE TEST

A test was developed to simulate the actual development of plaque and determine the effectiveness of a particular treatment in preventing the formation of plaque. The substrate used was thoroughly cleaned aluminum strips. The strips were immersed in wax simulated saliva, then transferred to a growth medium containing sucrose and an inoculum of 24-hour human plaque for at least 5 hours. Following this, the strips were immersed in a 1:1 mixture of saliva and test solution. The next treatments were:

(1) washing,
(2) incubation in dilute, centrifuged saliva,
(3) saliva-test agent,
(4) incubation in sucrose-plaque medium,
(5) saliva-test agent,
(6) incubation in saliva,
(7) incubation in medium with no added sucrose or plaque
(8) washing.

At the end of this procedure, the strips were sonicated in water to remove all plaque particles. The turbidity of the resulting suspensions were read at 570 nm using a Unicam S.P. 500 Spectrophotometer.

The results of the test are in Table I following:

TABLE I

| Conc Zn (ppm) in Saliva-Agent Mixture | % Inhibition Relative to 0% Zn | | |
|---|---|---|---|
| | Zn Citrate | Zn CMOS | Zn Sulfate |
| 2025 | 35±14 | 65±14 | 68±14 |
| 1013 | 27±14 | 51±14 | 50±14 |
| 410 | 23±14 | 43±14 | 43±14 |

Mean ± 95% confidence limits from 3 experiments each with 2 strips per treatment.

Zinc CMOS appears to be about as effective an antiplaque treatment as zinc sulfate and far more effective than insoluble zinc citrate. The comparability with zinc sulfate is surprising since the sulfate releases a large amount of free zinc ion in solution whereas the CMOS salt does not.

An in-vitro "dipping test" was used to simulate the production of dental calculus. The basic test is described in an article by S. Wah Leung, "A New Method for the In Vitro Production of Dental Calculus," J. Periodontology, 28:217 (1956), and is modified as described herein.

The creation of dental calculus was simulated on frosted glass plummets by continuously dipping them in a calcifying solution. Each dipping cycle consisted of a 30 second immersion in the solution followed by 30 seconds air drying. The dipping apparatus was enclosed in a constant temperature cabinet at 36° ± 1° C. at high humidity.

Daily anticalculus treatment consisted of 5 minutes dipping in distilled water, 1 minute immersion in a test solution and a 5 minute dipping in distilled water. Dipping in calcifying solution is then repeated.

The calcifying solution is made with porcine glycoprotein, which has similar properties to human mucin. Th submaxillary gland of a pig is minced, extracted three times with water in a Waring Blender, for five minutes each, stirred at low speed for 18 hours, centrifuged in 250 ml bottles at at least 15,000 G for 30 minutes and lyophylized in a Stoken Freezer Dryer for 2 days. All procedures were carried out at 4° C. The mucin is dessicated in 5 gm quantities at 40° C.

A new calcifying solution is prepared each day by adding the lypholized mucin to 135 ml $CaCO_3$ solution and 15 ml $PO_4$ buffer, then bubbling with $CO_2$ until the mucin dissolved. The $CaCO_3$ solution is prepared by adding 0.070 g $CaCO_3$ to 540 ml $H_2O$ and bubbling with $CO_2$ until the carbonate dissolves. The phosphate buffer (pH = 7) is a mixture of 8 g $NaH_2PO_4$ and 9.47 $Na_2HPO_4$ in a liter of water.

After 8 days of dipping, the plummets are dessicated for 24 hours at 40° C., and analyzed for calcium and phosphorus. The Ca/P ratio is determined and compared with the ratios for actual dental calculus, which vary from 1.28 to 1.55.

Results of this testing are reported in Table III below. The positive control is zinc chloride, a clinically tested anticalculus agent; the negative control is water.

TABLE II

| Compound | % Conc. (Wt./Vol.) | Ca/P |
|---|---|---|
| $H_2O$ | 100 | 1.30 |
| $Zn_3(CMOS)_2$ | 1.0 | 1.00 |
| $Zn_3(CMOS)_2$ | 0.5 | 1.06 |
| $Zn_3(CMOS)_2$ | 0.2 | 1.13 |

TABLE II-continued

| Compound | % Conc. (Wt./Vol.) | Ca/P |
|---|---|---|
| $ZnCl_2$ | 0.2 | 0.85 |

The results of this testing show zinc CMOS to be an effective anticalculus agent, but slightly less effective than zinc chloride.

ASTRINGENCY TEST

This was an actual determination of taste preference between zinc CMOS and zinc sulfate. Solutions of each were prepared, each containing 1% zinc. Three panelists each tested two portions of each solution given in random order and unmarked. Tap water was used to rinse out the mouth between samplings which were made with no effective lapsed time between them. Two out of the three panelists preferred zinc CMOS, finding it less astringent than zinc sulfate.

The test was further refined to provide for a ½ hour lapse between samplings. In addition to the water rinse, the panelists ate a "saltine"-type cracker to clear the palate. The pH of the zinc CMOS was adjusted from 5.2 to 5.9 with sodium CMOS, so that it was the same as zinc sulfate. Again, three panelists sampled each solution twice. All three preferred zinc CMOS. Typical comments were that it had a sweeter, almost fruity taste.

The minimum amount of the zinc compound necessary to result in a control of plaque and/or calculus is generally about 0.1% in the composition. While there is no maximum effective concentration, an amount significantly higher than about 1% will not provide any particular advantage. The particularly preferred concentration of the compound is about 0.1 to about 0.5 in a mouthrinse for application to plaque and/or calculus. The maximum concentration which can be utilized is properly determined by product parameters such as astringency and formulation compatibilities. A suitable pH is about 3 to about 7 and preferably about 4 to about 6.5 to deliver sufficient metal ions to the site of the plaque formation or calculus formation. A pH of about 5 to about 6.5 is optimum to accomplish application of zinc to the calculus or plaque. If the composition is too acidic it will attack the teeth and be more astringent and these effects must be kept in mind when formulating compositions of this invention.

In one embodiment, the invention comprises a water-alcohol soluble zinc CMOS mouthwash (oral rinse) which reduces dental plaque and calculus. In a further embodiment, the compounds of the invention may be used in a dentifrice. The essential components of the invention are an orally acceptable medium, which may be for example, water and alcohol, and the compound. The term "orally acceptable medium" applies to any suitable carrier medium for the compound; such a medium is selected to be harmless to the oral cavity and not meant to be intentionally swallowed. The medium is, of course, harmless in an amount accidentally ingested during use.

The compound of the instant invention may be utilized in a variety of oral products such as mouthwashes, toothpastes, dentifrices, tooth powders, lozenges, and chewing gum as well as in any compatible vehicle for applying the compound to the specific site of plaque formation. Such formulations being generally prepared in accordance with the art recognized practice.

In mouthwash formulations, for example, the medium includes typically an essentially aqueous solution of alcohol, glycerine or sorbitol. In some mouthwash formulations it is not essential to use any of these materials although they do help to solubilize certain flavor oils. A suitable mouthrinse, for example, contains about 0.1% of zinc carboxymethyloxysuccinate in a medium consisting essentially of 75–95% water and 5–25% ethanol. Other common additives may also be present.

In toothpastes and tooth powder formulations, the essential ingredient other than the zinc CMOS of this invention is a suitable dental abrasive. It is recommended that the abrasives used in the dentrifice formulation of the present invention provide a final composition which has an acceptable dentin abrasion value. Suitable dental abrasive substances include finely divided particles of appropriate size, hardness and composition for dentrifice abrasives.

Toothpastes and tooth powder formulations also commonly contain a soap or synthetic surface active agent. It is essential in these formulations as well as mouthwash formulations to provide sufficient foaming action to satisfy a market consumer preference for this property. A preferred material for dentifrices is sodium lauryl sulfate. However, many other surface active agents can be used.

In addition, the toothpaste formulation will frequently contain humectants sufficient to provide smooth texture and flowability. Glycerine and sorbitol are preferred for this purpose together with suitable amounts of water, ethyl alcohol, glucose and mannitol.

Lastly, the toothpaste formulation generally contains selected binding agents. These also should be compatible with the compound as well as with the other toothpaste components. For example, cellulose ethers are one type of preferred binder.

A chewing gum medium normally comprises a gum base and common flavoring materials used in the field. The flavoring materials are present at a level of about 0.01–2.0% of the final chewing gum composition. The base is a chewable plastic gum material such as natural rubber, chicle, polyvinyl acetate, ester gum, coumarone resin, and paraffin wax. The gum base is typically made from a mixture of two or more plastic gum materials to achieve a preferred degree of plasticity for chewing. Optionally, a binder or a softener may be used as well as sweetening agents.

Lozenges may be made containing the compound with a suitable binder.

The following Examples will more fully illustrate the embodiments of this invention. The pH of the compositions are adjusted as desired with HCl or NaOH. All parts and proportions referred to herein and in the appended claims are by weight unless otherwise noted.

EXAMPLE I — Mouthwash

| | |
|---|---|
| Ethanol | 22.00 |
| Glycerol | 12.00 |
| Flavor, color | 0.90 |
| Zinc carboxymethyloxysuccinate | 0.25 |
| Sodium lauryl sulfate | 0.10 |
| Polyoxyethylene 20 | 0.20 |
| Sorbitan monolaurate* | |
| Water | Balance to 100% |

*marketed by Hodag Chemical Company as Polysorbate 20.

EXAMPLE II — Tooth Powder

| | |
|---|---|
| Abrasive | 95.3 |
| Sodium lauryl sulfate | 3.0 |
| Zinc carboxymethyloxysuccinate | 0.3 |
| Flavor | 1.4 |
| | 100.0% |

EXAMPLE III — Toothpaste

| | |
|---|---|
| Particulate polishing agents | 10.00 |
| Humectant (sorbitol) | 40.00 |
| Sodium lauryl sulfate (21% glycerine) | 7.00 |
| Bodying agent (carboxymethylcellulose) | 1.00 |
| Flavor, color | 1.50 |
| Zinc carboxymethyloxysuccinate | 0.40 |
| Water | Balance to 100% |

EXAMPLE IV — Toothpaste

| | |
|---|---|
| Abravise | 13.00 |
| Binder | 0.30 |
| Sorbitol (70% solution) | 64.20 |
| Cab-O-Sil bodying agent | 8.50 |
| Polyethylene glycol, mw 6000 | 1.00 |
| Stannous Flouride | 0.30 |
| Zinc carboxymethyloxysuccinate | 0.25 |
| Sodium lauryl sulfate/glycerine | 7.00 |
| Flavor, color | 3.00 |
| Water | Balance to 100% |

EXAMPLE V — Mouthwash

| | |
|---|---|
| Zinc carboxymethyloxysuccinate | 0.36 |
| Flavor | 0.15 |
| Humectant | 8.00 |
| Saccharin | 0.02 |
| FD&C Yellow No. 6 | 0.10 |
| (0.7% solution) | |
| FD&C Red No. 2 | 0.12 |
| (0.2% solution) | |
| Sodium lauryl sulfate | 0.33 |
| Tween 20 | 0.30 |
| Water | Balance to 100% |

EXAMPLE VI — Toothpaste

| | |
|---|---|
| Abrasive | 10.00 |
| Zinc potassium carboxymethyloxysuccinate | 4.50 |
| Refined extract of carragheen | 0.35 |
| Titanium dioxide | 0.50 |
| Bodying Agent (Cab-O-Sil) | 9.00 |
| Saccharin | 0.20 |
| Glycerine (95%) | 60.00 |
| Polyethylene glycol, mw = 400 | 4.00 |
| 21% sodium lauryl sulfate in glycerine | 7.00 |
| Coloring and flavor | 1.32 |
| Water | Balance to 100% |

EXAMPLE VII — Toothpaste

| | |
|---|---|
| Abrasive | 15.00 |
| Powdered polyethylene[1] | 5.00 |
| Carboxymethylcellulose | 0.80 |
| Glycerine | 65.00 |
| Saccharin | 0.20 |
| Zinc sodium carboxymethyloxysuccinate | 10.25 |
| Flavor | 1.30 |
| Coloring | 0.25 |
| Foaming agent | 0.63 |

-continued

| | |
|---|---|
| Water | Balance to 100% |

(1) The polyethylene is a high density polyethylene powder having an average particle size of about 8-9 microns.

EXAMPLE VIII — Toothpaste

| | |
|---|---|
| Abrasive | 17.00 |
| Polyethylene powder(1) | 5.00 |
| Carboxymethylcellulose | 0.80 |
| Zinc ammonium carboxymethyloxysuccinate | 3.00 |
| Saccharin | 0.35 |
| Glycerine | 55.00 |
| Flavor | 1.30 |
| Foaming agent (sodium lauryl sulfate) | 1.47 |
| Color | 0.25 |
| Water | Balance to 100% |

(1) The polyethylene is a high density polyethylene powder having an average particle size of about 8-9 microns.

The invention has been described with respect to certain preferred embodiments and various modifications and variations in the light thereof will be suggested to persons skilled in the art and are to be included with the spirit and purview of this application and the scope of the appended claims.

What is claimed is:

1. A relatively non-astringent composition having a pH of about 7 or less for controlling plaque and calculus comprising as an active ingredient an effective amount to control said plaque and calculus of at least one compound or hydrate of a compound of the formula $$Zn_xM_y(CMOS)_n$$

wherein n is 1 or 2 and
(a) when n is 1, x and y are both 1 and M is $H^+$, $Na^+$, $K^+$, $Li^+$, $NH_4^+$ or a $C_{10}$ to $C_{18}$ alkyl substituted ammonium cation;
(b) when n is 2, x and y are independently 1 or 2 and the sum of x + y is 3 and M is $Ca^{++}$, $Mg^{++}$ or $Zn^+$ in admixture with an acceptable oral medium compatible with said compound or said hydrate.

2. A composition as defined in claim 1 wherein said effective amount is at least about 0.1% by weight.

3. A composition as defined in claim 1 wherein said pH is about 4 to about 6.5.

4. A composition as defined in claim 1 wherein said pH is about 5 to about 6.5.

5. A composition as defined in claim 1 said acceptable oral medium comprising water.

6. A composition as defined in claim 1 wherein said compound is $Zn_3(CMOS)_2$.

7. A composition as defined in claim 1 wherein said compound is $ZnNH_4(CMOS)$.

8. A composition as defined in claim 1 wherein said compound is $ZnH(CMOS)$.

9. A plaque and calculus controlling mouthrinse at a pH of about 3 to about 7 consisting essentially of at least 0.1% zinc CMOS in a medium consisting essentially of 75% to 95% water and 5% to 25% ethanol.

10. A method for controlling plaque and calculus comprising introducing to the site of said plaque or calculus at a pH of about 6.7 or less an effective amount to control said plaque or calculus of a compound or a hydrate of a compound of the formula $$Zn_xM_y(CMOS)_n$$

wherein n is 1 or 2 and
(a) when n is 1, x and y are both 1 and M is $H^+$, $Na^+$, $K^+$, $Li^+$, $NH_4^+$ or a $C_{10}$ to $C_{18}$ alkyl substituted ammonium cation;
(b) when n is 2, x and y are independently 1 or 2 and the sum of x + y is 3 and M is $Ca^{++}$, $Mg^{++}$ or $Zn^{++}$.

11. A method as defined in claim 10 wherein said pH is about 5 to about 6.

12. A method as defined in claim 10 wherein said compound is $Zn_3(CMOS)_2$.

13. A method as defined in claim 10 wherein said compound is $ZnNH_4(CMOS)$.

14. A method as defined in claim 10 wherein said compound is $ZnH(CMOS)$.

* * * * *